United States Patent [19]
Bar-Or et al.

[11] Patent Number: 5,833,716
[45] Date of Patent: Nov. 10, 1998

[54] ELECTRODE STRUCTURE AND SYSTEM

[75] Inventors: Jonathan Bar-Or, Mobile Post Menashe; Roger H. Nathan, Herzlia; Harold Weingarden, Raanana, all of Israel

[73] Assignee: N.E.S.S. Neuromuscular Stimulation Systems Ltd., Raanana, Israel

[21] Appl. No.: 547,531

[22] Filed: Oct. 24, 1995

[30] Foreign Application Priority Data

Oct. 25, 1994 [IL] Israel .......................................... 111396

[51] Int. Cl.⁶ ..................................................... A61N 1/04
[52] U.S. Cl. ........................... 607/149; 607/152; 607/153
[58] Field of Search .................................... 607/149, 152, 607/153, 139, 140; 602/2

[56] References Cited

U.S. PATENT DOCUMENTS 4,535,779  8/1985  Ober ........................................ 607/149

FOREIGN PATENT DOCUMENTS 1163803  10/1958  France ..................................... 607/152
2481924  11/1981  France ......................................... 602/2

*Primary Examiner*—Lee S. Cohen
*Attorney, Agent, or Firm*—Jacobson, Price, Holman & Stern, PLLC

[57] ABSTRACT

There is provided disposable, liquid-impregnable adhesive cloth pad for an electrode/skin interface, having a cloth pad impregnable with, and substantially retaining, an electrically conductive liquid and adapted to be mounted on selected locations on the skin of a patient, an electrically conductive electrode connectable to a stimulator for supplying stimulating impulses to the electrode, and a layer of an adhesive applied at least to a portion of the cloth pad, the layer serving to removably attach the pad to the electrode. There is also provided an electrode system, having a conductive member electrically connectable to a stimulator, an electrode in spaced-apart relationship with the conductive member, and a spring element providing an elastic, resilience-generated force ensuring an electrical contact between the conductive member and the electrode.

5 Claims, 2 Drawing Sheets

ELECTRODE STRUCTURE AND SYSTEM

FIELD OF THE INVENTION

The present invention relates to a disposable, water-impregnable adhesive cloth pad for an electrode/skin interface and to an electrode system for use with a rigid or semi-rigid exoskeleton such as a splint, sleeve or cuff, which provides the means to hold the electrode onto a body limb, for instance, for Functional Electrical Stimulation (FES) of paralysed muscles in spinal-cord lesion patients for restoration of hand movements.

BACKGROUND OF THE INVENTION

Surface stimulation electrodes generally interface with the skin through a layer of a conductive liquid or gel. Commercially available electrode gel, or water with some salt content, such as saline, or tapwater, are often used to provide this interface. The gel is generally spread over the electrode surface, which is then placed onto the skin. A porous structure is often used to contain the conductive liquid. Sponge pads, and various open-structure polymers have been used for this liquid-carrying layer. The liquid and its porous supporting structure require periodic changing due to contamination by perspiration and bacteria.

In prior art systems, not only is the proper positioning of the electrodes usually beyond the capabilities of the patient himself, but requires a considerable amount of time even of an expert. A further disadvantage of prior-art systems is the need to provide each electrode with a direct lead connecting it to the stimulator. This implies the attachment, to each electrode, of a delicate lead which is prone to become entangled during the positioning of the electrode or to become disconnected.

SUMMARY OF THE INVENTION

It is one of the objects of the present invention to provide a porous pad to serve as an electrode/skin interface, which pad holds a substantial amount of conductive liquid and is easily peeled off the electrode for replacement.

It is a further object of the present invention to provide an electrode system which allows the patient, without expert knowledge, to position an entire electrode array on his own arm in a matter of seconds.

It is still a further object of the invention to provide a system obviating the need to attach a lead to each electrode.

According to the invention, this is achieved by providing a disposable, liquid-impregnable adhesive cloth pad for an electrode/skin interface, comprising a cloth pad impregnable with, and substantially retaining, an electrically conductive liquid and adapted to be mounted on selected locations on the skin of a patient, an elecrically conductive electrode connectable to a stimulator for supplying stimulating impulses to said electrode, and at least one layer of an adhesive applied at least to a portion of said cloth pad, said at least one layer serving to removably attach said pad to said electrode.

According to another aspect of the invention, there is provided an electrode system comprising a conductive member electrically connectable to a stimulator, an electrode in spaced-apart relationship with said conductive member, and a spring element providing an elastic, resilience-generated force ensuring an electrical contact between said conductive member and said electrode.

The invention will now be described in connection with certain preferred embodiments with reference to the following illustrative figures so that it may be more fully understood.

With specific reference now to the figure in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE PREFERRED EMBODIMENTS

Figure 1:
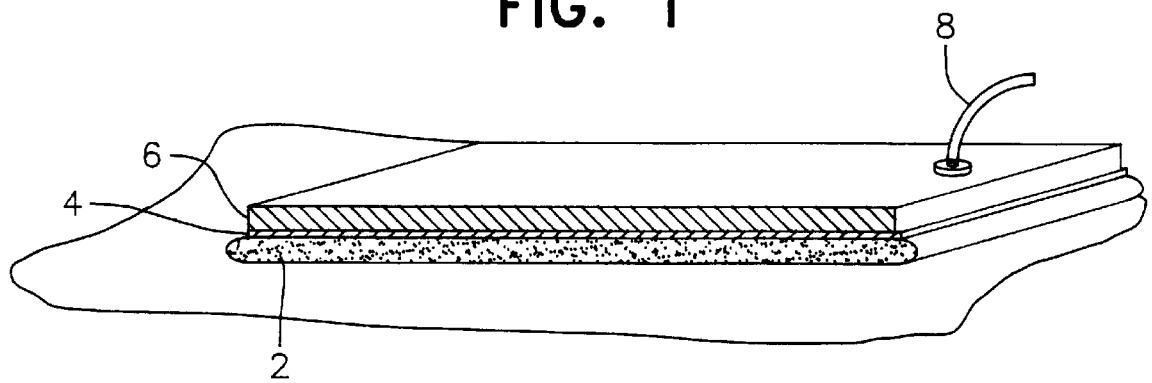
FIG. 1 is a perspective, partial cross-sectional view of the arrangement according to one embodiment of the invention.

Referring now to the FIG. 1, there is seen a water-soaked pad 2 made from non-woven cloth, and covered by an adhesive layer 4. The adhesive should allow the stimulation current to pass through it, being either conductive in itself, or by only partially covering the cloth, e.g., being arranged in a striped or a dotted pattern on the cloth surface, or as a border around the edge of the cloth pad. The adhesive itself retains its adhesive properties when the pad is saturated with water. Manual pressure applied to the adhesive 4 between the pad 2 and the surface of a conductive electrode 6 activates the adhesive properties of the layer 4, resulting in firm attachment of the pad 2 to the surface of electrode 6. When required, the pad 2 may be removed by manually peeling it off the electrode 6. The adhesive layer 4 is designed, by virtue of its greater adherence to the cloth pad 2 than to the electrode 6, to separate from the latter and to be disposed of with the pad 2. A fresh pad/adhesive can then be placed on the electrode 6. By means of a conductor 8, the electrode 6, advantageously a metal foil, is connected to the stimulator.

A further possibility for the intermediate adhesive layer 4 is the use of a compound layer, such that the properties of the adhesives are optimal for the two components they are required to glue together. For example, a commercial self-adhesive material (e.g., D-C-Fix, Konrad Hornschuch AG D-74679, Weissbach) can be glued to the cloth pad by a further cement (3M 90 High Strength Adhesive, 3M Co., St. Paul, Minn., U.S.A.). The resulting compound layer ensures permanent adhesion to the cloth layer 2, while constituting a light, reappliable adhesive for bonding to the electrode 6, or to any surface behind the electrode and supporting it.

Figure 2:
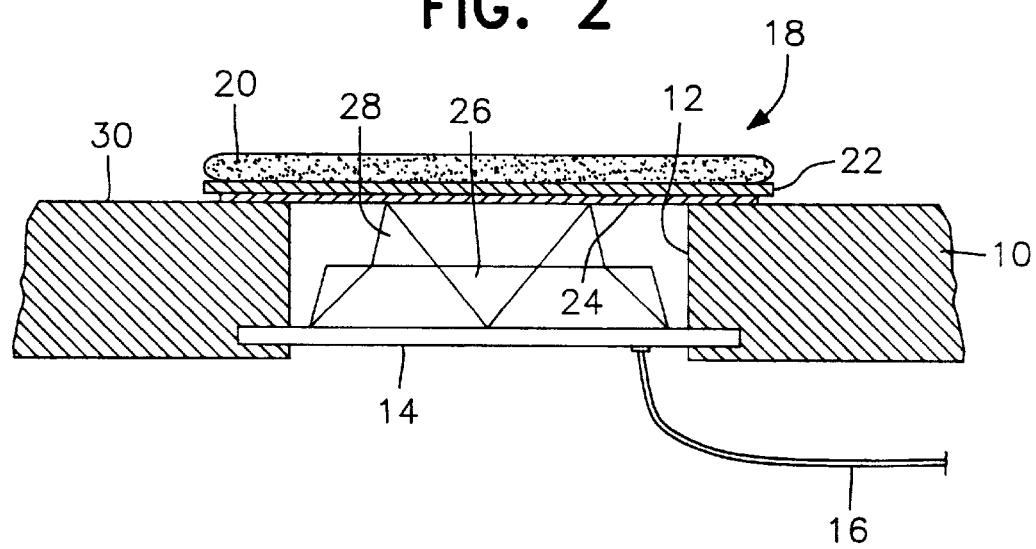
FIG. 2 is a schematic cross-section of the electrode system according to a second embodiment of the invention.

Referring now to the FIG. 2, there is seen, greatly magnified, a portion of the splint 10 in which an aperture or hole 12 has been provided in the estimated center of the region of the proposed electrode location. One side of the hole 12 is closed by a metallic disk 14 to which is attached a connecting wire 16 leading to the stimulator (not shown). Opposite the metal disk 14 there is mounted the electrode 18, which advantageously consists of three layers: a skincontacting pad 20 made of a fabric and capable of absorbing a conductive liquid, e.g., saline or even tap water, a substrate for the pad 20 in the form of a metal, e.g., brass foil 22 to which the pad 20 is removably attached with the aid of an electrically-conductive adhesive, and an adhesive tape 24 with two active faces, one of which sticks to metallic foil, and the other being used to attach the electrode 18 to the splint 10 at the desired position.

Figure 3:
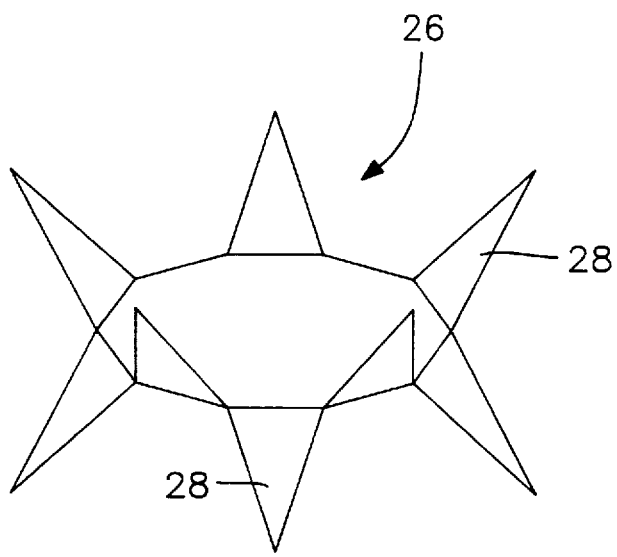
FIG. 3 is a perspective view of the star spring connector of the system shown in FIG. 2.

Before the electrode 18 is attached to the splint, however, the star spring connector 26 is inserted into the hole 12 in the splint 10. This connector 26 is in the form of an, e.g., 10-pointed star prepared from a spring material such as spring steel, of a thickness of about 0.1 mm. The legs 28 of the star spring are alternatingly bent slantingly upwards and downwards, as is clearly seen in the perspective drawing of FIG. 3. Its free height is such that, when inserted into the hole 12 its set of upper legs 28 protrudes beyond the surface 30 of the splint 10 by about 1 mm. When the electrode 18 is now glued to the splint 10 at the desired location and orientation, the star spring connector 26 is slightly compressed, the sharp points of its legs 28 penetrate the adhesive tape 24 and, due to its permanent reaction to the compressive force applied by the electrode 18 when elastically flexing the legs 28, establish a constant and reliable contact between the metal disk 14 connected to the stimulator and the metal foil 22 to which the pad 20 is attached.

Figure 4:
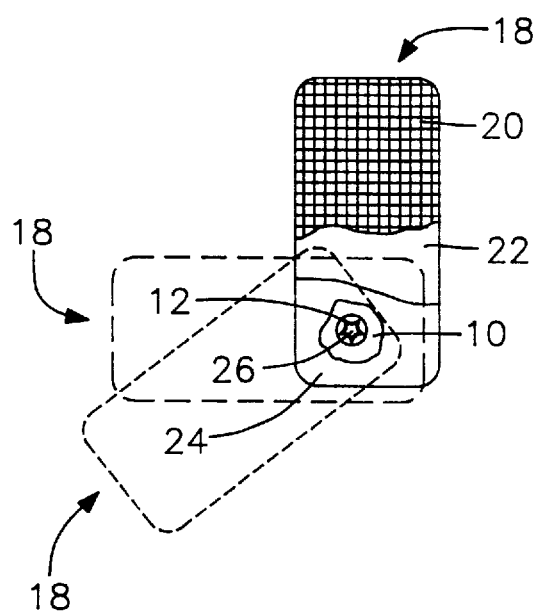
FIG. 4 shows an electrode in a number of possible locations and orientations on a splint.

FIG. 4 shows an electrode 18 in position as seen from the skin side. Part of the pad 20, the metal foil 22 and the adhesive tape 24 have been cut away to show the star spring connector 26 inside the hole 12 in the splint 10. Further seen are electrodes 18 in two of an infinity of alternative locations and orientations.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An electrode system, comprising:
    a conductive member electrically connectable to a stimulator;
    an electrode in spaced-apart relationship with said conductive member, and
    a spring element located between said electrode and said conductive member, and providing an elastic, resilience-generated force ensuring an electrical contact between said conductive member and said electrode,
    wherein said spring element has a star-like configuration consisting of a central, substantially disk-like shape and a plurality of pointed, peripheral legs integral with said central shape and bent in an outward slanting manner alternatingly towards one and towards the other side of said central shape, with the points of said pointed legs providing said electrical contact.

2. The electrode system as claimed in claim 1, wherein the free height of said spring element exceeds the distance between said conductive member and said electrode.

3. The electrode system as claimed in claim 1, wherein said electrode comprises a skin-touching fabric pad impregnable with a conductive fluid, a metal substrate to which said pad is removably attached by a first, electrically conductive, adhesive, and a second adhesive by which the pad-carrying substrate is attached to another surface.

4. In combination, an electrode system for functional electrical stimulation and an exoskeleton having an inner, skin-touching surface and an outer surface, comprising:
    at least one aperture provided in said exoskeleton in the region of a desired location of an electrode;
    a conductive member for each electrode, said member adapted to be in electrical connection with a stimulation device and being fixedly attached to said exoskeleton in such a way as to provide a conductive bottom to said aperture;
    a conductive spring element nested in said aperture and abutting against said conductive member; and
    at least one electrode for making electrical contact with a patient's skin, adapted to be attached to the inner surface of said exoskeleton, with at least part of its exoskeleton-facing surface covering said aperture and providing another abutment for said spring element.

5. The electrode system as claimed in claim 4, wherein the height of said spring element is larger than the depth of said aperture from said bottom to said inner surface, whereby said spring element is compressed when said electrode is attached to said inner surface, thereby ensuring electrical contact between said conductive number and said electrode.

* * * * *